(12) United States Patent
Allen et al.

(10) Patent No.: US 9,877,819 B2
(45) Date of Patent: Jan. 30, 2018

(54) PELVIC IMPLANT NEEDLE SYSTEM AND METHOD

(71) Applicant: Boston Scientific Scimed, Inc., Maple Grove, MN (US)

(72) Inventors: John J. Allen, Mendota Heights, MN (US); James R. Mujwid, Crystal, MN (US); Johannes N. Gaston, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/811,834

(22) Filed: Jul. 29, 2015

(65) Prior Publication Data
US 2015/0327974 A1    Nov. 19, 2015

Related U.S. Application Data

(63) Continuation of application No. 13/602,857, filed on Sep. 4, 2012.

(60) Provisional application No. 61/530,380, filed on Sep. 1, 2011.

(51) Int. Cl.
| | | |
|---|---|---|
| *A61F 2/04* | (2013.01) | |
| *A61F 2/00* | (2006.01) | |
| *A61B 17/34* | (2006.01) | |
| *A61B 17/06* | (2006.01) | |
| *A61B 17/00* | (2006.01) | |

(52) U.S. Cl.
CPC ...... *A61F 2/0063* (2013.01); *A61B 17/06109* (2013.01); *A61B 17/3476* (2013.01); *A61F 2/0045* (2013.01); *A61B 2017/0042* (2013.01); *A61B 2017/0046* (2013.01); *A61B 2017/00805* (2013.01); *A61F 2002/0072* (2013.01)

(58) Field of Classification Search
CPC ............. A61B 17/062; A61B 17/0625; A61B 2017/00349; A61B 2017/0047; A61B 2017/0472; A61B 2017/06066; A61B 2017/06085; A61B 2017/00805
See application file for complete search history.

(56) References Cited

U.S. PATENT DOCUMENTS

| | | | |
|---|---|---|---|
| 5,074,874 A * | 12/1991 | Yoon ................. | A61B 17/0469 606/139 |
| 2002/0026202 A1* | 2/2002 | Honey ................ | A61B 17/221 606/127 |
| 2003/0176875 A1* | 9/2003 | Anderson .......... | A61B 17/0401 606/151 |
| 2004/0098048 A1* | 5/2004 | Cunningham ... | A61B 17/06066 606/223 |
| 2004/0144395 A1 | 7/2004 | Evans et al. | |
| 2006/0015001 A1* | 1/2006 | Staskin .............. | A61B 17/3468 600/30 |
| 2009/0112258 A1* | 4/2009 | Kreidler .......... | A61B 17/06066 606/222 |

(Continued)

*Primary Examiner* — Charles A Marmor, II
*Assistant Examiner* — Thaddeus Cox
(74) *Attorney, Agent, or Firm* — Brake Hughes Bellermann LLP

(57) ABSTRACT

Various embodiments of a trocar or needle system for use in inserting and deploying pelvic implants are provided. The needle device can include a solid or hollow shaft portion with a non-circular cross-section. A grip element can be provided to slide along a length of the needle shaft to further facilitate handling.

8 Claims, 4 Drawing Sheets

(56) References Cited

U.S. PATENT DOCUMENTS

| | | | | |
|---|---|---|---|---|
| 2010/0217069 A1* | 8/2010 | Meade | ............... | A61B 17/0485 600/37 |
| 2011/0270281 A1* | 11/2011 | Malkowski | .......... | A61B 17/062 606/147 |
| 2012/0065461 A1* | 3/2012 | Chu | ................. | A61B 17/06109 600/37 |

* cited by examiner

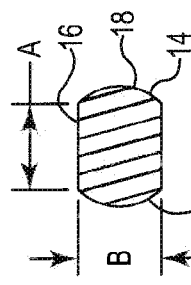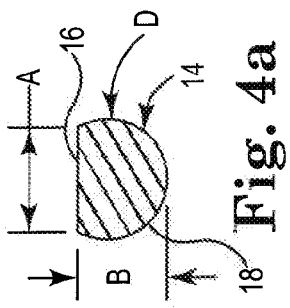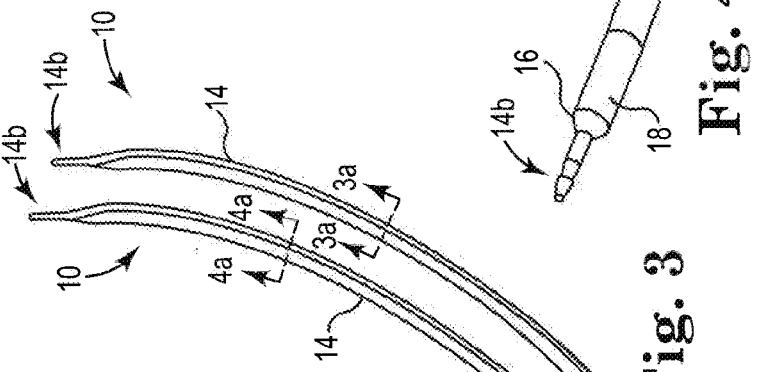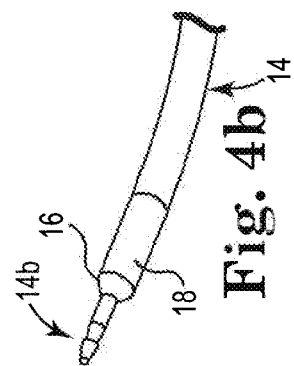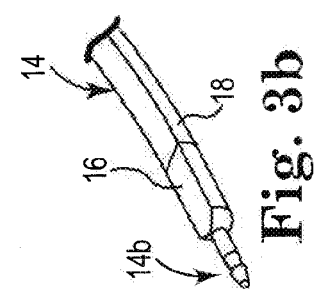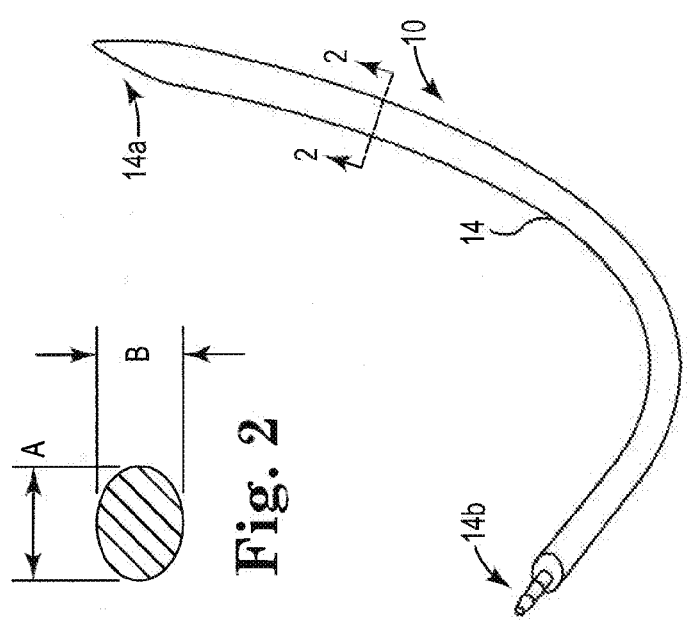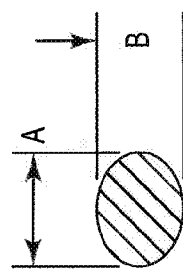

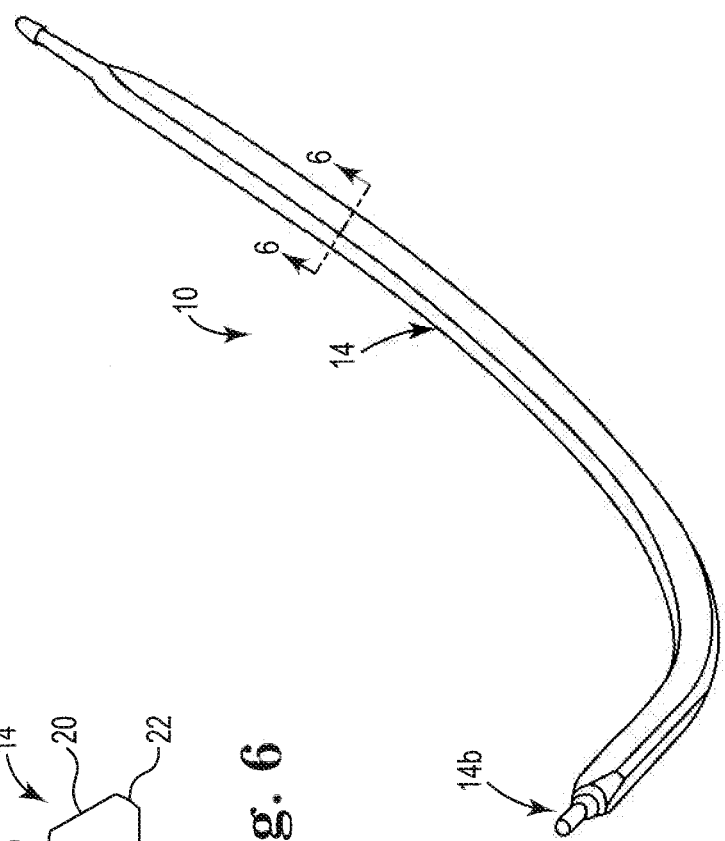
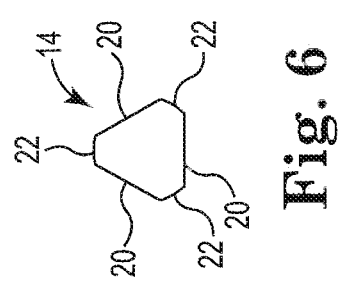

PELVIC IMPLANT NEEDLE SYSTEM AND METHOD

PRIORITY

This Application is a Continuation Application of U.S. patent application Ser. No. 13/602,857, filed Sep. 4, 2012, which claims priority to and the benefit of U.S. Provisional Patent Application No. 61/530,380, filed Sep. 1, 2011; each of which is incorporated fully herein by reference.

FIELD OF THE INVENTION

The present invention relates generally to surgical methods and apparatus and, more specifically, to surgical trocar or needle devices used for introducing and deploying an implant or sling to treat incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implant and introduction system that can be used to treat incontinence, and/or pelvic organ prolapse and other conditions.

SUMMARY OF THE INVENTION

The present invention describes an implant or sling insertion needle or trocar system, device and method. While typical trocars can include a curved stainless steel needle to create a pathway for a supporting mesh sling, embodiments of the present needle device can include a solid or hollow needle shaft portion with a non-circular cross-section. The use of a non-circular form for the needle provides distinct functional advantages.

Namely, a needle device having a non-circular cross-section needle shaft can provide improved visual and tactile feedback pertaining to the orientation of the needle, better gripping control of the needle, and improved finger contact surfaces to reduce finger pressure and slippage.

Embodiments can include a needle device having a housing or grip element. The grip can be constructed of a rigid plastic material, suitably shaped for gripping by the physician's fingers. The grip element can include flats, curved portions, holes, a through-aperture or other constraining means by which it may be slidably attached to the needle. In certain embodiments, for instance, the through-aperture is shaped and sized to generally match the shape and size of the needle, e.g., non-circular cross-section. As such, the grip element can slide along a longitudinal length of the non-circular cross-section needle, while still restricting rotational movement about the needle shaft. A mechanism can be included with the element, e.g., button or actuator, to selectively stop sliding of the element along the needle when desired. The mechanism allows the physician to apply both axial and rotational loads on the needle.

The needles described and depicted herein can be employed in treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Implants utilized with the system can include a tissue support portion and one or more anchors, arms and the like.

Embodiments of the present invention may be incorporated into or provided with various commercial products marketed by American Medical Systems of Minnetonka, Minn., as the MiniArc® Single-Incision Sling and like implant or anchoring systems.

BRIEF DESCRIPTION OF THE DRAWINGS

FIG. 1 is a schematic view of a non-circular, generally elliptical, needle device, in accordance with embodiments of the present invention.

FIG. 2 is a schematic cross-sectional view of the non-circular, generally elliptical, needle device of FIG. 1, in accordance with embodiments of the present invention.

FIG. 3 is a schematic view of a non-circular needle device, with flat and curved portions, in accordance with embodiments of the present invention.

FIG. 3a is a schematic cross-sectional view of the non-circular needle device of FIG. 3, in accordance with embodiments of the present invention.

FIG. 3b is a partial schematic view of a non-circular needle device, with flat and curved portions, in accordance with embodiments of the present invention.

FIG. 4 is a schematic view of a non-circular needle device, with flat and curved portions, in accordance with embodiments of the present invention.

FIG. 4a is a schematic cross-sectional view of the non-circular needle device of FIG. 4, in accordance with embodiments of the present invention.

FIG. 4b is a partial schematic view of a non-circular needle device, with flat and curved portions, in accordance with embodiments of the present invention.

FIG. 5 is a schematic view of a non-circular trilobe needle device, in accordance with embodiments of the present invention.

FIG. 6 is a schematic cross-sectional view of the non-circular trilobe needle device of FIG. 5, in accordance with embodiments of the present invention.

DETAILED DESCRIPTION OF PREFERRED EMBODIMENTS

Figure 7:
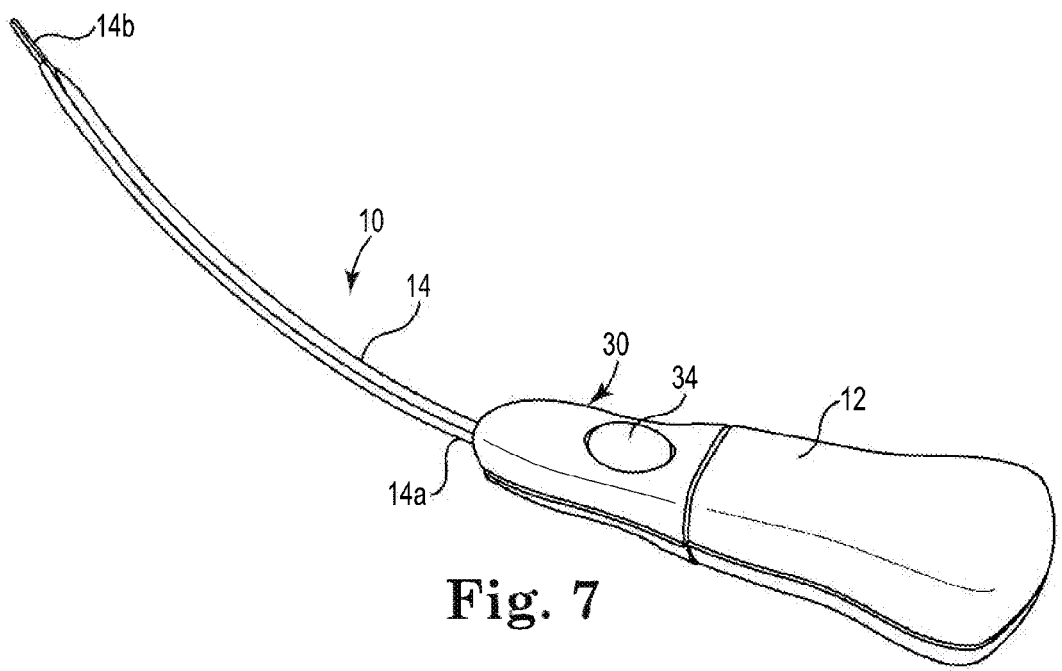
FIG. 7 is a schematic view of a needle device having a needle shaft, handle and slidable grip element, in accordance with embodiments of the present invention.

Referring generally to FIGS. 1-10, various embodiments of a trocar or needle device 10 are shown. The needle device 10 described and depicted herein can be employed in introducing or deploying implants used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Implants utilized with the system can include a tissue support portion and one or more anchors, arms and the like, as disclosed herein.

The needle devices 10 can include a handle portion 12 and a needle portion 14. The needle portion 14 can be curved, straight, helical, and the like. The needle portion 14 can include a proximal portion 14a and a distal tip portion 14b. The proximal portion 14a can be operatively connected to the handle portion 12.

The needle 14 of the present invention can include a solid or hollow shaft with a non-circular cross-section. The use of a non-circular form for the needle 14 provides distinct functional advantages. Namely, a non-circular cross-section needle 14 provides improved visual and tactile feedback pertaining to the orientation of the needle, better gripping control of the needle, and improved finger contact surfaces to reduce finger pressure and slippage. In addition, defined flat or angular surfaces along portions of the needle 14 shaft can provide a desirable construct to restrict rotation of any device or mechanism adapted to slide along a length of the needle 14.

Referring generally to FIGS. 1-6, the non-circular form of the needle 14 can take on numerous shapes and configurations. For instance, in one embodiment, the cross-section can be generally elliptical, as shown in FIGS. 1-2. Such a generally elliptical structure can be defined by a horizontal dimension A and a vertical dimension B. In certain embodiments, dimension A can be defined in a range of approximately 0.150 inches to 0.200 inches, with dimension B defined in a range of approximately 0.100 inches and 0.150 inches. Other dimensional characteristics can be employed with various embodiments without deviating from the spirit and scope of the present invention.

As shown in FIGS. 3-4b, embodiments of the needle 14 can include one or more flat portions 16 and one or more curved portions 18 to define the non-circular needle cross-section. The one or more curved portions 18 can be generally concave, convex, or a combination thereof. The one or more flat portions 16 can facilitate and promote contact and stability for the physician's finger to provide orientation feedback and granular control. The flat portions 16 can face either toward the inside or outside of the needle bend, for those embodiments having a curved needle 14. The horizontal portion A can be defined in a range of approximately 0.150 inches to 0.175 inches, with the vertical dimension B defined in a range of approximately 0.125 inches to 0.150 inches. Again, other dimensional characteristics can be employed with various embodiments without deviating from the spirit and scope of the present invention. FIGS. 4-4b depict an embodiment having a single flat portion 16 and a larger single curved portion 18, e.g., 0.175 inch to 0.200 inch diameter D. FIGS. 3-3b show an embodiment having two opposing flat portions 16 and two opposing curved portions 18. The flat portions 16 can be approximately 0.125 inches to 0.140 inches in length, with the vertical dimension B ranging approximately between 0.120 inches and 0.140 inches. Again, other dimensional characteristics, proportions and shapes are envisioned for various embodiments.

FIGS. 5-6 show an embodiment of the needle 14 having a generally trilobe configuration or cross-section. The trilobe configuration can be defined by three primary linear portions 20. In certain embodiments, the linear portions 20 are in direct communication to define a generally triangular shape. In other embodiments, as shown in FIG. 6, one or more secondary portions 22 extend between the linear portions 20. The secondary portions 22 can be generally linear or curved. For those embodiments having generally curved portions 22 the diameter D measurement for one or more of the portions 22 can range from approximately 0.175 inches to 0.190 inches. Again, other dimensional characteristics are envisioned for use as well. These various trilobe embodiments can provide a desirable tactile feedback and control structure for the needle 14 as well.

Other triangular, rectangular, octagonal, hectagonal, pentagonal, and like shapes and constructs, including other polygon shapes, can be implemented to achieve one or more non-circular needle 14 cross-sections to facilitate the objectives and advantages described herein.

Figure 8:
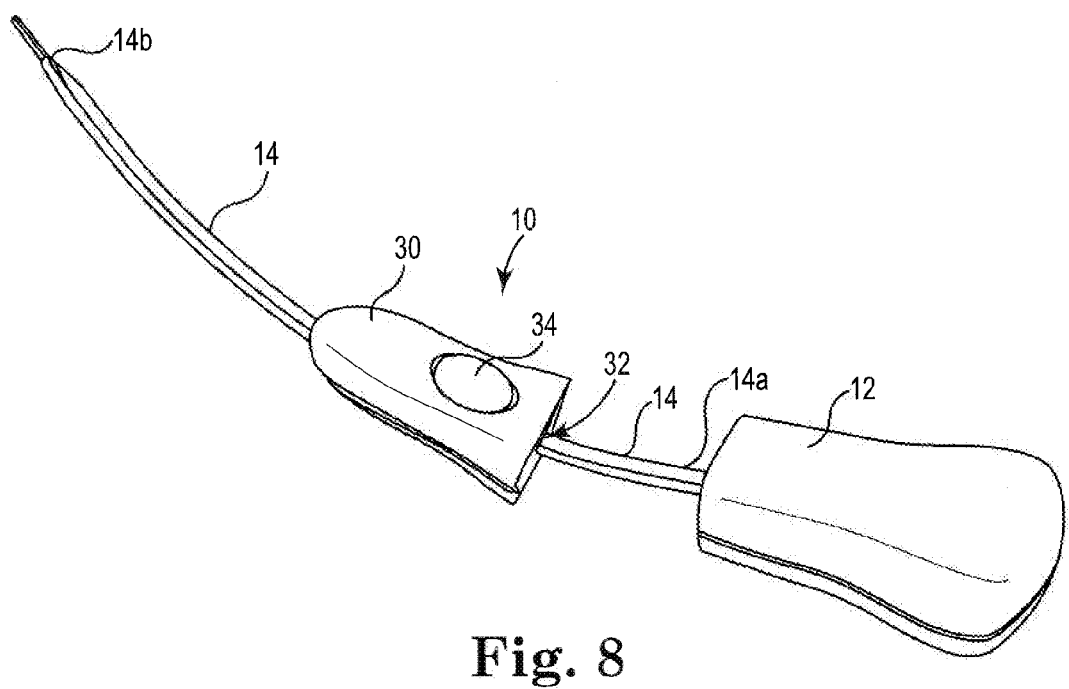
FIG. 8 is a schematic view of a needle device having a needle shaft, handle and slidable grip element slid a distance along a length of the shaft, in accordance with embodiments of the present invention.

FIGS. 7-8 show and describe various exemplary use applications for the needle device 10 having a housing or grip element 30. Again, the needle 14 can be connected to the handle 12. In certain embodiments, the grip 30 is constructed of a rigid plastic material, suitably shaped for gripping by the physician's fingers and/or hand. The outer portions of the grip 30 can include various surface textures or features to further faciliate handling and gripping.

The grip element 30 can include flats, curved portions, holes, a through-aperture 32 or other constraining means by which it may be slidably attached to the needle 14. In certain embodiments, for instance, the through-aperture 32 is shaped and sized to generally match the shape and size of the needle 14 (except it can be measurably larger to permit sliding along the needle 14), e.g., non-circular cross-section. As such, the grip element 30 can slide along a longitudinal length of the non-circular cross-section needle 14, while still restricting rotational movement about the needle shaft. A mechanism 34 can be included with the housing 30, e.g., button or actuator, to selectively stop sliding of the element 30 along the needle 14 when desired. The mechanism 34 can be a stop member, ratchet mechanism, a friction feature or element or like mechanism operatively connected with the mechanism 34. Such a mechanism 34 can be in operative communication with a rubber member or element adapted for selective engagement with the needle shaft. The mechanism 34 allows the physician to apply both axial and rotational loads on the needle 14 during implant introduction or deployment.

In certain embodiments, the grip element 30 can be employed with a needle 14 having a generally circular cross-section. Further, various embodiments of the mechanism 34 can be initially biased or engaged with the needle to restrict sliding of the grip 30 along the needle 14 until the mechanism 34 is actuated or released.

To use the device 10, a physician or end user actuates or releases the mechanism 34 to permit slidable repositioning of the element 30 along the needle 14. When at the desired position, the stop mechanism 34 is re-engaged, or released, to allow the physician to apply both axial and rotation loads to the needle 14. This element 30 can be particularly useful with "top-down" or like retropubic needle passes in which the physician commonly manipulates the needle 14 directly rather than via the handle 12.

Alternatively, the element 30 can serve as a bearing surface particularly useful when passing a needle through the anatomical structure during a "bottom-up" implantation procedure. With the mechanism 34 disengaged, the device 10 may be held in one hand while the other hand is free to push the needle from the handle. With curved needles 14, this allows the needle to advance along its curved shape without pushing into or dragging along the hand holding the needle.

Figure 9:
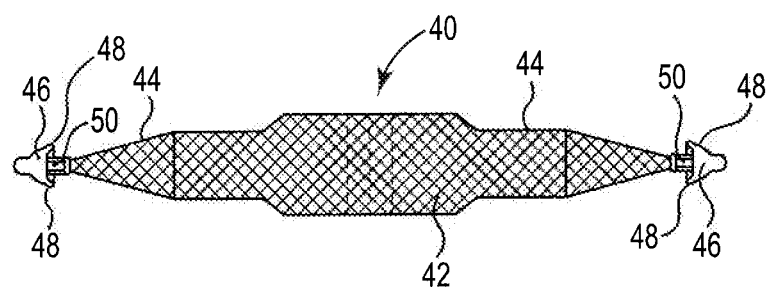
FIGS. 9-10 are schematic views of pelvic implant devices for use with needle devices, in accordance with embodiments of the present invention.
Figure 10:
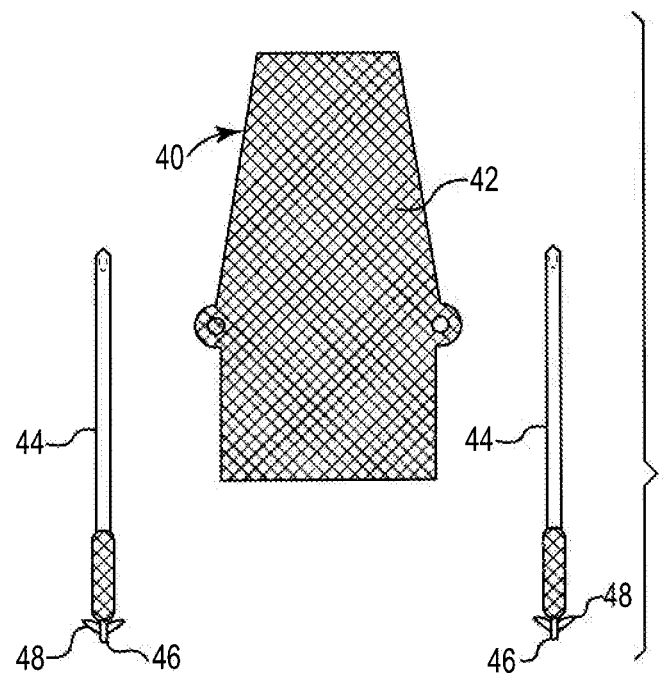

As shown in FIGS. 9-10, various embodiments of implantable sling or mesh devices 40 and methods adapted to include certain anchoring and other implant structures or devices are disclosed herein for use with the present invention. In general, the implant devices 40 can include a support portion 42, and extension or arm portions 44 having anchors 46 provided therewith. Various anchor 46 embodiments provided herein can include one or more extending tines or barbs 48 to promote tissue engagement and fixation. An aperture or other engagement portion 50 can be included with the device 40, e.g., the anchors 46, and adapted to selectively or releasably engage with the device 10, e.g., the needle tip 14b. Various portions of the implant device 40 can be constructed of polymer materials from a mesh of filaments. Certain embodiments can be constructed of or from a film or sheet material of polypropylene, polyethylene, fluoropolymers or like compatible materials.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2012/0157761, 2011/0144417, 2011/0124956, 2010/0105979, 2002/151762 and 2002/147382. Accordingly, the above-identified disclosures are fully incorporated herein by reference in their entirety.

The implant systems, tools, devices, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the systems, devices, device portions, components or structures disclosed herein can be constructed of compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant introduction system, comprising:
  an implant introduction device, including;
    a handle having a handle abutment portion having a peripheral edge;
    a needle having a distal tip, and a curved shaft defining a needle bend, the curved shaft having a first side, and a second side opposite to the first side, the first side being flat, the second side being curved, the first side of the curved shaft facing towards an inside of the needle bend;
    a gripping device configured to slide along a length of the curved shaft, and having:
      a gripping abutment portion having a peripheral edge substantially matching a size and shape of the peripheral edge of the handle abutment portion;
      an actuation button configured to selectively control sliding of the gripping device along the curved shaft;
      a lumen having a cross-sectional shape that matches a cross-sectional shape of the curved shaft, and configured to receive the curved shaft to restrict rotational movement about the curved shaft; and
  an implant having a support portion, a first arm portion, and a second arm portion, the implant having a first anchor coupled to the first arm portion, and a second anchor coupled to the second arm portion, the first anchor defining an aperture configured to receive the distal tip of the needle.

2. The system of claim 1, wherein the implant is a mesh sling.

3. The system of claim 1, wherein at least the shaft of the needle is constructed of metal.

4. The system of claim 1, wherein the curved shaft includes a third side, and a fourth side opposite to the third side, the third side being curved, the fourth side being curved.

5. The system of claim 4, wherein the second side, the third side, and the fourth side, collectively, define a semi-circle shape.

6. The system of claim 1, wherein, when the actuation button is pressed, the actuation button is configured to stop a sliding of the gripping device, wherein, when the actuation button is released, the gripping device is configured to slide along the length of the curved shaft.

7. The system of claim 1, wherein the first arm portion and the second arm portion are separate constructs from the support portion.

8. An implant introduction system, comprising:
  an implant introduction device, including;
    a handle having a handle abutment portion having a peripheral edge;
    a needle having a distal tip, and a curved shaft defining a needle bend, the curved shaft having a first side, and a second side opposite to the first side, the first side being flat, the second side being curved, the cross-sectional shape of the curved shaft having a horizontal dimension in a range of approximately 0.150 inches to 0.175 inches and a vertical dimension in a range of approximately 0.125 inches to 0.150 inches;

a gripping device configured to slide along a length of the curved shaft, and having:
- a gripping abutment portion having a peripheral edge substantially matching a size and shape of the peripheral edge of the handle abutment portion;
- an actuation button configured to selectively control sliding of the gripping device along the curved shaft;
- a lumen having a cross-sectional shape that matches a cross-sectional shape of the curved shaft, and configured to receive the curved shaft to restrict rotational movement about the curved shaft; and an implant having a support portion, a first arm portion, and a second arm portion, the implant having a first anchor coupled to the first arm portion, and a second anchor coupled to the second arm portion, the first anchor defining an aperture configured to receive the distal tip of the needle.

\* \* \* \* \*